United States Patent [19]

Makler

[11] Patent Number: 4,585,438
[45] Date of Patent: Apr. 29, 1986

[54] DEVICE FOR INJECTING MATERIAL DIRECTLY INTO UTERINE CAVITY

[76] Inventor: Amnon Makler, 50 Disraeli Street, Ahuza, Haifa, Israel, 34334

[21] Appl. No.: 484,907

[22] Filed: Apr. 14, 1983

[51] Int. Cl.⁴ .............................................. A61M 29/00
[52] U.S. Cl. ...................................... 604/106; 604/55; 604/187; 128/17
[58] Field of Search ................... 604/55, 187, 106, 41; 128/17

[56] References Cited

U.S. PATENT DOCUMENTS

| | | | |
|---|---|---|---|
| 3,320,948 | 5/1967 | Martin | 604/106 X |
| 3,636,940 | 1/1972 | Gravlee | 604/41 X |
| 3,796,211 | 3/1974 | Kohl | 604/55 X |
| 4,071,027 | 1/1978 | Meador | 604/55 |
| 4,100,923 | 7/1978 | Southern | 604/55 |
| 4,119,098 | 10/1978 | Bolduc et al. | 604/55 |
| 4,325,387 | 4/1982 | Helfer | 604/55 X |

FOREIGN PATENT DOCUMENTS 2025232  1/1980  United Kingdom ................. 128/17

Primary Examiner—Michael H. Thaler
Attorney, Agent, or Firm—Bachman & LaPointe

[57] ABSTRACT

A semi-rigid tubular member for insertion into the uterine canal and preferably into the uterine cavity through which fluid may be injected, sealing structure communicating with the tubular member for sealing the external orifice of the cervical canal, and a syringe communicating with said tubular member for holding material to be injected. The device is particularly useful for effectively injecting a small volume of concentrated spermatozoa directly into the uterine cavity without irritation.

10 Claims, 9 Drawing Figures

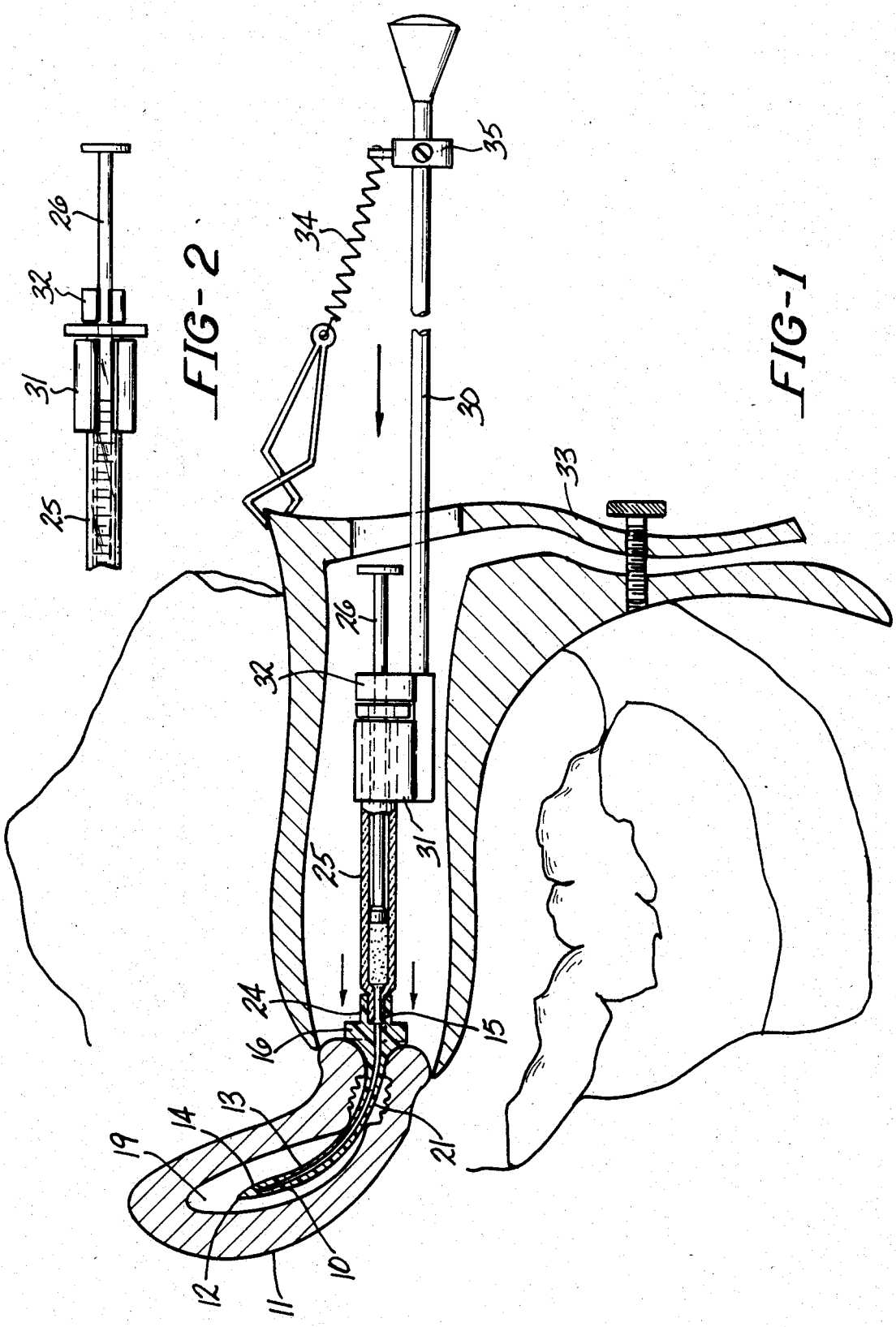

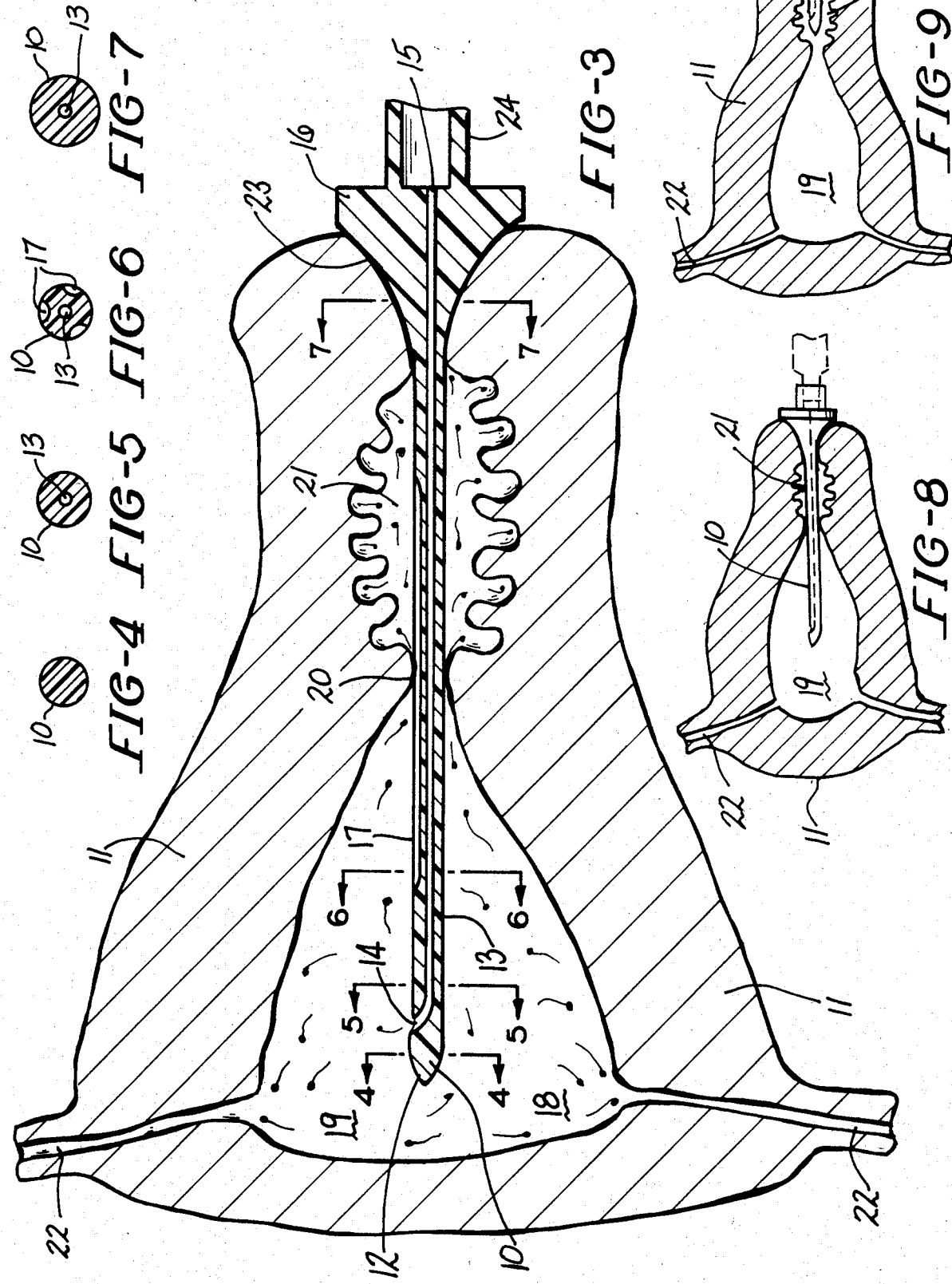
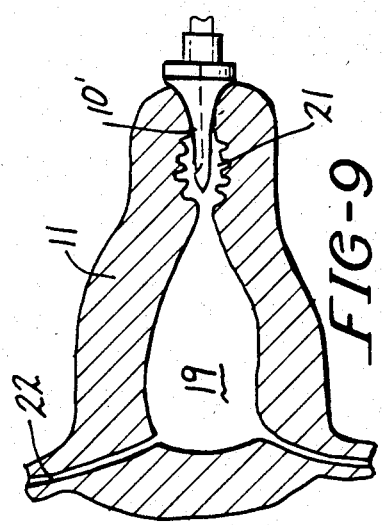
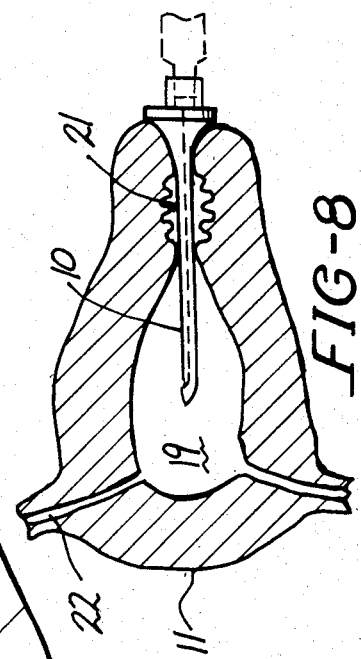

DEVICE FOR INJECTING MATERIAL DIRECTLY INTO UTERINE CAVITY

BACKGROUND OF THE INVENTION

The present invention relates to a medical device for safely and effectively injecting material directly into the uterine cavity. Devices of this type are useful for a variety of purposes especially for injecting a small volume of concentrated spermatozoa directly into the uterine cavity. Typical prior art devices are shown in U.S. Pat. Nos. 4,089,337, 4,126,134 and 4,119,098.

Art devices, however, may require the use of a tenaculum which may be painful and cause bleeding or other injury to the patient. Alternatively, art methods may require sealing of the cervical canal by insertion of a sealing means inside the uterine cavity which may also represent a painful procedure and also block access of the contents into the cervical canal. In addition, art devices may have a large dead space and therefore cannot operate effectively when only a small amount of material is available.

Accordingly, it is a principal object of the present invention to provide a device for injecting material directly into the uterine cavity and allow the material to be retained in both the uterine cavity and the cervical canal.

It is a further object of the present invention to provide a device as aforesaid which is safe and effective and is easy to use without trauma.

Further objects and advantages of the present invention will appear hereinafter.

SUMMARY OF THE INVENTION

The foregoing objects and advantages may be readily obtained in accordance with the present invention. The device comprises a semi-rigid tubular member or cannula for insertion into the uterine canal and preferably into the uterine cavity through which fluid may be inserted, sealing means communicating with said tubular member for sealing the external orifice of the cervical canal, and a syringe communicating with said tubular member for holding material to be injected. A resilient means, such as a spring, is preferably provided for retaining the sealing means in sealing engagement with the external orifice of the cervical canal. When the cannula is inserted directly into the uterine cavity, it is preferably grooved to allow access to the cervical canal.

BRIEF DESCRIPTION OF THE DRAWINGS

The present invention may be more readily understood from a consideration of the following illustrative drawings in which:

FIG. 1 is a side sectional view of the device of the present invention operatively disposed;

FIG. 2 is a partial top view of the syringe and holder;

FIG. 3 is an enlarged top sectional view showing the cannula operatively disposed;

FIGS. 4, 5, 6 and 7 are sectional views along lines 4—4, 5—5, 6—6 and 7—7 of FIG. 3, respectively;

FIG. 8 is a top sectional view of the cannula operatively disposed showing approximate actual size; and FIG. 9 is a top sectional view of a foreshortened cannula operatively disposed showing approximate actual size.

DETAILED DESCRIPTION

As indicated hereinabove, the present invention is useful for injecting any material directly into the uterine cavity. However, the present invention is particularly useful for injecting a small volume of concentrated spermatozoa directly into the uterine cavity and therefore the present invention will be discussed hereinafter with regard to this particularly advantageous application.

The major causes of infertility include low sperm concentration by the husband (oligospermia), low rate of sperm mobility (asthenospermia), or both. In certain cases sperm penetration into the wives' cervical canal is impaired by unfavorable cervical mucus.

In most cases semen of oligospermic or asthenospermic men fail to improve by systemic treatment. As an alternative, insemination by concentrated spermatozoa from such specimens is widely used. This treatment includes concentrating the spermatozoa by centrifugation and finally condensing them into a minute volume of about 0.3 cc. In this way the sperm concentration is increased several fold. Following this, the concentrated spermatozoa should be inseminated as close as possible to the location of the ova, that is, injected directly into the uterine cavity or at the least, injected into the cervical canal.

There are several important requirements for effective injection of concentrated spermatozoa. These requirements are admirably met by the device of the present invention. Thus, it should be possible to deposit the available minute volume without losing a significant portion of it within the dead space of the injective system. The device should be provided with a non-traumatic introducer or cannula that can be penetrated smoothly between the foldings of the cervical canal into the uterine cavity. Such a cannula should be semi-rigid to fit itself to the specific curvature of the uterus, and the device should not require the use of traumatic means such as a tenaculum. The injecting system should be provided with an effective and non-traumatic plugging mechanism. This is necessary to prevent back-flow of the injected contents resulting from the tendency of the uterus to contract when irritated by a foreign medium. It is important that the injected contents be retained within the uterine cavity and also have access to the cervical canal for as long as possible. A certain amount of time is necessary for the sperm to get into the Fallopian tubes or be stored in the foldings of the cervix from which they can thereafter be released to the uterine cavity and the Fallopian tubes.

The device of the present invention effectively achieves all of the foregoing goals. It provides a minimum amount of dead space within the injecting system, e.g., less than about 0.1 cc. It provides a semi-rigid, atraumatic cannula that can be smoothly penetrated into the cervical canal and into the uterine cavity itself without damage to the uterus and without the necessity for the use of a tenaculum. Also, the device of the present invention provides a simple, non-traumatic plugging mechanism to retain sperm in the uterine cavity and cervical canal and to prevent flow of the contents out of the cervix back to the vagina.

Referring to FIGS. 1 and 3, the cannula 10 is made of semi-rigid material so that it is flexible enough to bend with the natural curvature of the uterus 11 without damaging the uterus as shown in FIG. 1 but rigid enough to maintain its shape. Plastic materials such as polyvinyl chloride, polyethylene, polypropylene, polycarbonates and the like are preferred. The cannula is preferably 1.5-2 mm thick and either 12-17 mm long (short version 10' shown in FIG. 9) or 40-60 mm long (long version 10 shown in FIGS. 1, 3 and 8). The short version is intended for intracervical deposition for those women that cannot tolerate intrauterine insemination.

The cannula 10 is provided with a tapered, curved anterior end 12 and a central passageway 13 running the entire length of the cannula with an exit orifice 14 about 1-2 mm behind curved end 12 and an inlet orifice 15 at the enlarged posterior end 16. The outer surface of the cannula 10 is provided with one or more longitudinal grooves 17, with three such grooves being preferred as shown in FIG. 6. The longitudinal grooves 17 preferably run from behind exit orifice 14 and terminate before enlarged posterior end 16 to enable sperm 18 to migrate from the uterine cavity 19 through the internal orifice of the cervical canal 20 down to the cervical canal 21 as shown in FIG. 3. This feature usefully enables the sperm 18 to contact the cervical canal 21 and pick up cervical fluid which may assist the sperm capacitation in its passage in Fallopian tubes 22. The enlarged posterior end 16 becomes a wide cone blocking the external orifice of the cervical canal 23 having a base of a diameter of about 10-14 mm and terminates in flanges 24 to accept the tip of an ordinary 1 cc elongated tuberculine syringe 25 having conventional plunger 26.

A metal or plastic holder 30 is provided for holding syringe 25 and tubular member 10 provided with clamp means for holding the syringe firmly in place, such as upstanding flanges 31 and 32 engaging syringe 25 permitting free movement of plunger 26. Holder 30 can, for example, be about 180-220 mm long and about 3-4 mm thick. Adjustable speculum 33 is preferably employed to provide easy access to the vagina. Resilient means, such as spring 34, is preferably employed to urge syringe 25 and enlarge posterior end of tubular member 16 into sealing engagement with the external orifice of the cervical canal 23. Adjustable member 35 is provided on holder 30 and spring 34 is engaged between the speculum 33 and member 35 thereby enabling adjustment of the tension. Naturally, other resilient means may be provided that serve the same purpose.

The operation of the device of the present invention is as follows. The tubular member 10 is fixed to syringe 25 by flanges 24 and 0.2-0.3 cc of the concentrated sperm are aspirated into the syringe. The syringe containing sperm and tubular member affixed thereto is placed in clamp 31, 32 of holder 30. Speculum 33 is introduced into the vagina, holder 30, syringe 25 and tubular member 10 inserted therein and the tubular member inserted into the uterine cavity 19 via cervix 21 until the external orifice 23 is blocked by the base 16 of the tubular member as shown in FIG. 1. Due to the shape and flexibility of the tubular member, a tenaculum to grasp and pull the uterus to an elongated shape is not required and bleeding and pain are avoided. The tubular member readily follows the natural curvature of the uterus without damage thereto and without damage to the cervical canal or folding thereof. Spring 34 is fastened with the aid of a clamp on the brim of the speculum 33 and on the adjustable member 35 and the desired tension set by sliding member 35 along holder 30. The contents of syringe 25 are injected through the tubular member into the uterine cavity and circulate throughout the uterine cavity and into the cervical canal via grooves 17. A certain amount of sperm swim towards the Fallopian tubes while the rest can be stored in the foldings of the cervical canal as a reservoir and also mix with the cervical fluid. Sealing means 16 is pressed firmly against the external orifice of the cervical canal and held in place by resilient means 34. This acts as a retainer and prevents any back-flow of the contents throughout the entire duration of the treatment, i.e., 15-20 minutes, during which time the patient is left alone. Thereafter the device is removed and the patient discharged.

It can be readily seen that the device of the present invention offers many advantages. Thus, the device is non-traumatic and can be readily used without pain or bleeding. There is a virtual absence of dead space. A tenaculum for grasping the uterus is not required. The sealing means need not be inserted into the uterus, i.e., the sealing means effectively seals the uterus by sealing the external orifice of the cervical canal. The grooved cannula enables access to the cervical canal. An alternative device is available for patients who cannot tolerate interuterine injection. The device is simple and easy to use without complications.

This invention may be embodied in other forms or carried out in other ways without departing from the spirit or essential characteristics thereof. The present embodiment is therefore to be considered as in all respects illustrative and not restrictive, the scope of the invention being indicated by the appended claims, and all changes which come within the meaning and range of equivalency are intended to be embraced therein.

What is claimed is:

1. A device for injecting material directly into the uterine cavity of the non-pregnant uterus which comprises: a semi-rigid tubular member for insertion into the uterine canal through which fluid may be injected; sealing means communicating with said tubular member for sealing the external orifice of the cervical canal including an enlarged base portion of said tubular member which sealingly fits into the external orifice and tightly seals said external orifice, said sealing means and tubular member permitting free circulation of said fluid in the uterine cavity and uterine canal; a syringe communicating with said tubular member for holding the fluid to be injected; a speculum for insertion into the vagina in cooperation with said syringe; and a resilient means engaged with said speculum for retaining said sealing means in sealing engagement with the external orifice of the cervical canal by urging said resilient means into sealing engagement with the external orifice of the cervical canal, wherein said device has a minimum amount of dead space less than about 0.1 cc.

2. A device according to claim 1 wherein said resilient means is a spring.

3. A device according to claim 1 including a holder for holding said syringe, wherein said sealing means is supported by said holder and wherein said resilient means engages said holder.

4. A device according to claim 3 including a speculum for insertion into the vagina with the holder inserted into the speculum, wherein said resilient means is engaged between said holder and speculum and urges said sealing means into sealing engagement with the external orifice of the cervical canal.

5. A device according to claim 1 wherein said sealing means is integral with said tubular member.

6. A device according to claim 5 wherein said sealing means is adjacent said syringe to enable fluid to be injected directly into said tubular member.

7. A device according to claim 1 wherein said tubular member has a tapered, curved anterior end and an enlarged posterior end, with a central passageway having an inlet orifice at the posterior end and an exit orifice behind the anterior end.

8. A device according to claim 1 wherein said sealing means is fixedly secured to said tubular member.

9. A device according to claim 1 including means associated with said tubular member to permit circulation of said fluid between said uterine cavity and uterine canal.

10. A device for injecting material directly into the uterine cavity of the non-pregnant uterus which comprises: a semi-rigid tubular member suitable for insertion into both the uterine canal and uterine cavity through which fluid may be injected including at least one longitudinal groove terminating before the end thereof to permit access from the uterine cavity to the uterine canal; sealing means communicating with said tubular member for sealing the external orifice of the cervical canal including an enlarged base portion of said tubular member which sealingly fits into the external orifice and tightly seals said external orifice, said sealing means and tubular member permitting free circulation of said fluid in the uterine cavity and uterine canal; and a syringe communicating with said tubular member for holding the fluid to be injected.

* * * * *